United States Patent
Rhême (10) Patent No.: US 10,288,911 B2
(45) Date of Patent: May 14, 2019

(54) DEVICE FOR EMISSION OF POLARIZED LIGHT AND ITS DETECTION HAVING A POLARIZER WITH BREWSTER'S ANGLE TO PRODUCE POLARIZATION STATE IN DEFLECTED LIGHT

(71) Applicant: Optosys SA, Corminboeuf (CH)

(72) Inventor: Charles Rhême, Posieux (CH)

(73) Assignee: OPTOSYS SA (CH)

( * ) Notice: Subject to any disclaimer, the term of this patent is extended or adjusted under 35 U.S.C. 154(b) by 102 days.

(21) Appl. No.: 15/512,902

(22) PCT Filed: Oct. 12, 2015

(86) PCT No.: PCT/EP2015/073571
§ 371 (c)(1),
(2) Date: Mar. 21, 2017

(87) PCT Pub. No.: WO2016/058994
PCT Pub. Date: Apr. 21, 2016

(65) Prior Publication Data
US 2017/0293166 A1    Oct. 12, 2017

(30) Foreign Application Priority Data
Oct. 15, 2014   (EP) ..................................... 14189103

(51) Int. Cl.
*G01S 7/499* (2006.01)
*G02F 1/01* (2006.01)
(Continued)

(52) U.S. Cl.
CPC ........... *G02F 1/0136* (2013.01); *G01N 21/21* (2013.01); *G01S 7/4812* (2013.01); *G01S 7/4813* (2013.01);
(Continued)

(58) Field of Classification Search
CPC ....... G01N 21/21; G01S 7/4812; G01S 7/499; G01S 17/02; G01V 8/12; G02F 1/0136
(Continued)

(56) References Cited

U.S. PATENT DOCUMENTS 4,902,125 A * 2/1990 Keene ..................... G01S 7/481
356/28.5
6,618,132 B1   9/2003 Vann ......................... 356/141.1
(Continued)

FOREIGN PATENT DOCUMENTS

EP   0 349 343 A2   1/1990
EP   1 059 510 A1   12/2000
(Continued)

OTHER PUBLICATIONS

International Search Report dated Dec. 10, 2015 in corresponding PCT International Application No. PCT/EP2015/073571.
(Continued)

*Primary Examiner* — Que Tan Le
(74) *Attorney, Agent, or Firm* — Ostrolenk Faber LLP (57) ABSTRACT

A device for emission of polarized light and its detection including a light emitter configured to generate an outgoing light beam directed along an optical emission axis, a light receiver configured to detect an incoming light beam directed along an optical detection axis, and a polarization unit positioned in the optical emission axis and optical detection axis and configured to polarize the outgoing light beam and the incoming light beam. To allow a compact assembly, the device, by reducing the number of its constituent parts and by providing a good detection reliability of the device, the optical emission axis and the optical detection axis are angled with respect to one another such that they include an intersection point and the polarization unit includes a polarizer configured to deflect light from at least
(Continued)

one of the incoming light beam towards the optical detection axis and the outgoing light beam away from the optical emission axis, the deflected light being defined by a polarization state produced by the polarizer.

11 Claims, 7 Drawing Sheets

(51) Int. Cl.
    *G01N 21/21*      (2006.01)
    *G01V 8/12*      (2006.01)
    *G01S 7/481*      (2006.01)
    *G01S 17/02*      (2006.01)

(52) U.S. Cl.
    CPC .............. *G01S 7/499* (2013.01); *G01S 17/02* (2013.01); *G01V 8/12* (2013.01)

(58) Field of Classification Search
    USPC ................................................ 250/225, 216
    See application file for complete search history.

(56) References Cited

U.S. PATENT DOCUMENTS

| | | | |
|---|---|---|---|
| 8,830,581 B2 * | 9/2014 | Dewa ..................... | G01N 21/33 |
| | | | 359/320 |
| 2009/0073442 A1 | 3/2009 | Smith ........................... | 356/367 |
| 2009/0108185 A1 | 4/2009 | Hoersch et al. .............. | 250/225 |
| 2010/0007863 A1 | 1/2010 | Jordanoska ..................... | 355/53 |

FOREIGN PATENT DOCUMENTS

| | | |
|---|---|---|
| EP | 1 205 763 A1 | 5/2002 |
| EP | 2 508 920 A1 | 10/2012 |
| JP | 2000-097634 A | 4/2000 |

OTHER PUBLICATIONS

Written Opinion dated Dec. 10, 2015 in corresponding PCT International Application No. PCT/EP2015/073571.

* cited by examiner

DEVICE FOR EMISSION OF POLARIZED LIGHT AND ITS DETECTION HAVING A POLARIZER WITH BREWSTER'S ANGLE TO PRODUCE POLARIZATION STATE IN DEFLECTED LIGHT

CROSS-REFERENCE TO RELATED APPLICATIONS

The present application is a 35 U.S.C. §§ 371 national phase conversion of PCT/EP2015/073571, filed Oct. 12, 2015, which claims priority to European Patent Application No. 14189103.6, filed Oct. 15, 2014, the contents of which are incorporated herein by reference. The PCT International Application was published in the English language.

TECHNICAL FIELD

The invention relates to a device for emission of polarized light and its detection. The device comprises a light emitter configured to generate an outgoing light beam directed along an optical emission axis and a light receiver configured to detect an incoming light beam directed along an optical detection axis. The device further comprises a polarization unit positioned in the optical emission axis and optical detection axis which is configured to polarize the outgoing light beam and the incoming light beam.

BACKGROUND OF THE INVENTION

Such a device is known from publication no. EP 2 508 920 A1. As further described in this publication, the light emitter of the device emits light to a retroreflector reflecting the light back to the light receiver. Substantially no light stemming from any diffusing matter, such as white paper, or from any reflecting matter apart from the retroreflector shall be detected by the device. In order to reduce the detection of such diffused and reflected light to a large extent, the polarization unit of the device is equipped with two polarizers, wherein the emitted light is polarized by one polarizer and the light to be detected is polarized by the other polarizer. Both polarizers yield a differing polarization of the light passing through. The retroreflector causes a depolarization of the arriving light and emits it back in the same direction.

An application of the device is a detection of objects crossing the light path in between the retroreflector and the light receiver, in particular of objects comprising a section that is transparent or translucent in the visible light spectrum. The detection is based on an output signal generated by the device in dependence of light detected or not detected by the light receiver indicating the absence or presence of an object within a monitoring area.

The previously disclosed device, however, has a number of shortcomings. On the one hand, the polarization unit includes two different polarizers respectively accounting for a polarization of the outgoing light beam and a differing polarization of the incoming light beam. A twofold supply of those components represents a considerable cost factor, even more so when the components must match to a desired ultraviolet wavelength range. It also leads to a rather complex composition and manufacturing of the device. The provision of two polarizers arranged at different positions in the device can also negatively affect the detection reliability.

SUMMARY OF THE INVENTION

It is an object of the present invention to remedy at least one of the above mentioned disadvantages and to propose a device for an emission and detection of polarized light requiring a reduced number of components and/or allowing a more compact assembly of its constituent parts. It is another object to provide such a device with an increased detection reliability and/or detection sensitivity.

At least one of these objects is achieved with a device comprising the features disclosure herein. Advantageous embodiments of the invention are defined herein.

Accordingly, in a device according to the invention, the optical emission axis and the optical detection axis are angled with respect to one another such that they comprise an intersection point. Moreover, the polarization unit comprises a polarizer configured to deflect light from the outgoing light beam away from the optical emission axis and/or the incoming light beam towards the optical detection axis, wherein the deflected light is defined by a polarization state produced by the polarizer. In this way, a redirection of the light beam in order to distinguish between the outgoing light and incoming light for a reliable detection and to account for a different position at which the light emission and light detection process take place in the device can be advantageously accomplished by the polarizer itself. This can be exploited for a less intricate composition of the device and/or for a reduction of needed components.

Preferably, the polarizer is configured to transmit light in a direction towards the light receiver and/or away from the light emitter. The transmitted light preferably comprises light defined by a polarization state produced by the polarizer which is preferably differing from the polarization state produced by the polarizer in the deflected light. Thus, the polarizer may be advantageously applied to produce a polarization state both on the outgoing light and on the incoming light contributing to a further decrease of required components and/or a facilitated buildup of the device.

Preferably, the polarization states produced in the deflected light and in the transmitted light are orthogonal to one another. Thus, a criterion for an unambiguous distinction between the outgoing light and the incoming light can be provided by means of the orthogonal polarization states which can be exploited for a high detection reliability.

Preferably, the polarizer is configured to produce at least one of a linear polarization state, a circular polarization state, and an elliptical polarization state in at least one of the deflected light and the transmitted light. According to a preferred configuration, the polarization state produced in the deflected light corresponds to an s-polarization. The differing polarization state produced in the transmitted light preferably corresponds to a p-polarization. This configuration can enable a rather uncomplicated and reliable implementation of the inventive concept.

Preferably, the light receiver is configured to detect light in an ultraviolet (UV) wavelength range, preferably including at least an ultraviolet C (UVC) wavelength range or an ultraviolet B (UVB) and ultraviolet C (UVC) wavelength range. In particular, preferably a wavelength range below 350 nm, more preferred below 300 nm, and most preferred below 290 nm is detectable by the light receiver. The light receiver is preferably a photodiode.

Preferably, the light emitter is configured to emit light in an ultraviolet (UV) wavelength range, more preferred in an ultraviolet B (UVB) and ultraviolet C (UVC) wavelength range, and most preferred in an UVC wavelength range. In particular, preferably a wavelength range below 350 nm, more preferred below 300 nm, and most preferred below 290 nm is emitted by the light emitter. Preferably, the light emission spectrum of the light emitter is substantially restricted to this wavelength range. Preferably, the light emitter comprises a light emitting diode (LED) and/or a laser diode. In particular, the light emitter may be provided such that it emits a divergent light beam traveling along the optical emission axis. Preferably, the divergent light beam is narrowed by at least one lens to a substantially parallel light beam traveling along the optical emission axis.

An application of the device operating in this wavelength range can be in particular useful for a detection of objects comprising a section that is transparent or translucent in the visible light spectrum. These objects may include, for instance, glass bottles, plastic bottles, pharmaceutical vials, plastic packaging, and transparent foils. A preferred arrangement and method for the detection of such objects in which the device can be advantageously applied is disclosed in EP 2 508 921 A1 which is herewidth included by reference.

Preferably, the polarizer comprises a light receiving body adapted to receive a light beam. A fraction of the received light beam is preferably deflected from the light receiving body by producing a polarization state in the deflected light beam. Preferably, another fraction of the received light beam is transmitted through the light receiving body by producing a differing polarization state in at least a portion of the transmitted light beam. Preferably, the polarizer substantially consists of the light receiving body.

Preferably, the polarizer comprises a light receiving body utilizing Brewster's angle to produce the polarization state in the deflected light. A polarizer of such a kind can offer several key advantages including reduced costs, a high reliability over a comparatively large wavelength range, in particular including an UV wavelength range, a reduction of additionally required components, and a less complicated integration with respect to other components. The light receiving body is preferably formed by a plate. The material of the light receiving body preferably comprises a material transparent to UV light, more preferred UVC light. In particular a plastics material and/or glass, more preferred fused silica glass, is conceivable.

According to a first preferred configuration, the light receiving body of the polarizer is substantially transmissible over the complete wavelength range of the light emitted by the light emitter. According to a second preferred configuration, the light receiving body is wavelength selective and only allows a transmission over a portion of the wavelength range of the light emitted by the light emitter. Preferably, the transmissible wavelength range of the light receiving body comprises or consists of a UV wavelength range, more preferred a UVB and UVC wavelength range, and most preferred a UVC wavelength range. In particular, a wavelength range below 350 nm, more preferred below 300 nm, and most preferred below 290 nm is conceivable.

Preferably, the light receiving body of the polarizer comprises at least one layer of a dielectric coating, in particular a thin film of a dielectric material. The dielectric coating is preferably applied on at least one surface of the light receiving body. More preferred, several layers of a dielectric coating are positioned on top of each other. The dielectric coating can advantageously contribute to achieve a substantially unique polarization of the transmitted light, in particular such that a fraction as large as possible of the transmitted light is defined by a polarization state differing from the polarization state of the deflected light. This can contribute to a further improvement of the detection reliability. Such a light receiving body, in particular glass, comprising at least one dielectric coating can be advantageously applied in particular for light at a wavelength range below 300 nm for which other polarizers, such as plastic polarizers, are less efficient.

Fractions of the light transmitted through the polarizer defined by varying polarization states may be quantitatively determined by the extinction ratio. The extinction ratio can be determined as the ratio between the intensity of the light transmitted through the polarizer which is defined by the differing polarization state and the intensity of the remaining light being transmitted through the polarizer. In particular, the extinction ratio of the polarizer may be determined as the ratio between the intensity of p-polarized light Tp and of s-polarized light Ts transmitted through the polarizer, i.e. Tp/Ts. Preferably, the extinction ratio of the polarizer is at least 20, more preferred at least 100, and most preferred at least 200.

Preferably, an angle between a line perpendicular to the surface of the polarizer and at least one of the optical emission axis and the optical detection axis does not deviate by more than 5°, more preferred by more than 2°, from Brewster's angle. In this way, a high detection sensitivity or at least a detection sensitivity sufficient for specific applications can be ensured.

According to a preferred configuration, the polarizer is configured to transmit light in a direction of at least one of towards the light receiver and away from the light emitter in a substantially coaxial or parallel direction with respect to at least one of the optical detection axis and the optical emission axis. According to another preferred configuration, the polarizer is configured to transmit light in a direction towards the light receiver, wherein an optical axis along which the transmitted light beam substantially propagates deviates from the orientation of the optical detection axis by a deviation angle. According to a further preferred configuration, the polarizer is configured to transmit light in a direction away from the light emitter, wherein an optical axis along which the transmitted light beam substantially propagates deviates from the orientation of an external optical emission axis of a detectable outgoing light beam by a deviation angle. Also a combination of these configurations is conceivable.

According to a preferred implementation, the outgoing light beam is deflected by the polarizer away from the optical emission axis towards an external optical emission axis and the incoming light beam is transmitted through the polarizer towards the light receiver, in particular in a substantially coaxial or parallel direction with respect to the optical detection axis or along an optical axis deviating from the orientation of the optical detection axis by a deviation angle. According to another preferred implementation, the incoming light beam is deflected by the polarizer from an external optical detection axis towards the optical detection axis and the outgoing light beam is transmitted through the polarizer away from the light emitter, in particular in a substantially coaxial or parallel direction with respect to the optical emission axis and/or along an optical axis deviating from the orientation of an external optical emission axis of a detectable outgoing light beam by a deviation angle.

Preferably, the device comprises a reflector configured to reflect the outgoing light beam. The reflector is preferably configured such that an external light path of the outgoing light beam extends along an external optical emission axis between the polarizer and the reflector. Moreover, the reflector is preferably configured such that an external light path of a light beam reflected by the reflector extends along an external optical detection axis between the reflector and the polarizer. According to a preferred implementation, the external optical emission axis and the external optical detection axis substantially coincide and are substantially constituted by a single external optical axis. In this implementation, an angle enclosed between the external optical axis and a reflecting surface of the reflector preferably substantially corresponds to a right angle. According to another conceivable implementation, the external optical emission axis and the external optical detection axis do not coincide. In this implementation, an angle enclosed between the external optical emission axis and a reflecting surface of the reflector preferably deviates from a right angle. Correspondingly, an angle enclosed between the external optical detection axis and a reflecting surface of the reflector may deviate from a right angle.

Preferably, a collimator lens is positioned in between the light emitter and the polarizer. The collimator lens is preferably applied to narrow the light beam produced by the light emitter along its propagation direction on the emission axis. More preferred, a substantially parallel light beam is produced by the collimator lens. In this way, the coverage range of the outgoing light beam and thus also the detection response for the respective incoming light beam can be increased. In particular, a parallel, more preferred coaxial, propagation along the optical axis of the external light path before and/or after a reflection on the reflector is preferably produced by the collimator lens. Thus it can be ensured that a fraction as large as possible of the emitted light arrives in a substantially parallel beam shape at the polarizer.

Preferably, the optical emission axis substantially extends through an optical center of the collimator lens. In particular, the arrangement of the collimator lens can be employed to ensure that substantially all the light rays collimated by the collimator lens are impinging on the polarizer at substantially the same angle, in particular Brewster's angle. In this way, an outgoing light beam comprising or substantially consisting of the light reflected on and/or transmitted through the polarizer of substantially homogeneous properties and thus high quality can be produced. Preferably, the device is configured such that the substantially parallel light beam provided by the collimator lens is transmitted through and/or reflected on the polarizer, in particular before it is reflected on said reflector. Preferably, the collimator lens is provided in such a way that the optical emission axis substantially extends in parallel, more preferred coaxial, with respect to the substantially parallel light beam produced by the collimator lens.

Preferably, a focusing lens is positioned in between the polarizer and the light receiver. In this way, the detection sensitivity can be increased by ensuring that a fraction as large as possible of the light arriving at the polarizer is collected by the light receiver. In particular, a substantially parallel light beam on the polarizer produced by the collimator lens is preferably narrowed down by the focusing lens, thus optimizing the detection reliability. Preferably, the device is configured such that the substantially parallel light beam produced by the collimator lens is reflected on said reflector and/or is transmitted through and/or reflected on the polarizer before it is narrowed down by the focusing lens.

Preferably, the optical detection axis substantially extends through an optical center of the focusing lens. Preferably, the focusing lens is applied such that the incoming light beam is focused on the light receiver such that a major part of the incoming light or substantially all the incoming light is detectable by the light receiver. Preferably, the focusing lens is provided in such a way that the optical detection axis substantially extends in parallel, more preferred coaxial, with respect to the substantially parallel light beam produced by the collimator lens and/or reflected on said reflector.

Preferably, the optical emission axis and/or optical detection axis is defined by the orientation of the collimator lens and/or focusing lens. Preferably, the optical emission axis substantially extends through the optical center of the collimator lens and/or the optical detection axis substantially extends through the optical center of the focusing lens. The optical emission axis and/or optical detection axis preferably corresponds to the respective optical axis of the collimator lens and/or focusing lens. According to a preferred configuration, the collimator lens and/or focusing lens are provided by at least one plastic lens. In particular, the plastic lens may be fabricated by means of injection molding. The application of such a plastic lens may at least partially depolarize the outgoing and/or incoming light beam. An advantage of the above described arrangement according to the invention is that the use of such a depolarizing plastic lens is feasible. Thus, the overall production costs can be reduced as compared to a device in which glass lenses are employed. According to another preferred configuration, the collimator lens and/or focusing lens are provided by at least one glass lens.

Preferably, the light emitter and the light receiver are arranged in a common housing. Preferably, the housing substantially has a cuboid shape to provide a compact format of the device and a facilitated handling. Preferably, at least one of the optical emission axis and the optical detection axis substantially extends in parallel to a plane of at least one outer wall of the housing in order to permit an easier installation and alignment of the device in a detection setup.

Preferably, a pivotable fixation arm is projecting from a corner region and/or an outer edge of the housing in order to allow a facilitated installation and adjustment during an alignment of the device with respect to a monitoring area. The housing preferably also comprises a power adapter to provide electrical power for the included components and at least one signal output for a measuring signal.

Preferably, the housing comprises at least one window transparent for at least one of the outgoing light beam and the incoming light beam. More preferred, a single window for the outgoing light beam and the incoming light beam is provided. The window is preferably arranged at an outer edge of the housing. Preferably, at least one of the optical emission axis and the optical detection axis is substantially directed perpendicular to the window, which is further contributing to an intuitive optical geometry of the device in order to facilitate its installation.

According to a first preferred configuration, the window is substantially transparent over the complete wavelength range of the light emitted by the light emitter. According to a second preferred configuration, the window is wavelength selective and only allows a transmission over a portion of the wavelength range of the light emitted by the light emitter. Preferably, the transmittable wavelength range of the window comprises or consists of a UV wavelength range, more preferred a UVB and a UVC wavelength range, and most preferred a UVC wavelength range. In particular, a wavelength range below 350 nm, more preferred below 300 nm, and most preferred below 290 nm is conceivable.

According to a preferred implementation, an angle enclosed between the optical emission axis and the optical detection axis at the intersection point deviates from an angle of 180° twice subtracted by Brewster's angle by a deviation angle of at least 1°. More preferred, the deviation angle is at least 2°, most preferred at least 2.5°. In this way, the detection reliability of the device can be enhanced. In this implementation, the window is preferably provided in such a way that an angle enclosed between a surface of the window transmitted by at least one of the outgoing light beam and the incoming light beam and at least one of the optical emission axis and the optical detection axis deviates from a right angle substantially by the deviation angle. This can contribute to a facilitated installation of the device in a monitoring area.

According to another preferred implementation, an angle enclosed between the optical emission axis and the optical detection axis at the intersection point substantially corresponds to an angle of 180° twice subtracted by Brewster's angle. In this way, the detection sensitivity of the device may be enhanced.

Preferably, an intersection point of the optical emission axis and the optical detection axis is located inside the housing. The polarizer is preferably arranged in proximity to the intersection point. In particular, the intersection point is preferably located closer to the polarizer than to the light emitter and/or light receiver. More preferred, the polarizer is substantially arranged at the intersection point. In this way, a substantially identical optical path of the outgoing light and incoming light outside the housing along an external optical axis can be provided. This can also contribute to a facilitated installation of the device in a monitoring area, to a facilitated alignment of the outgoing light beam and incoming light beam, and thus to a better detection reliability.

Preferably, the polarizer is tilted with respect to the optical emission axis and the optical detection axis. Preferably, an angle between the optical emission axis and a surface of the polarizer at which the outgoing light beam is deflected and/or transmitted does not deviate by more than 10°, more preferred by more than 3°, from an angle between the optical reception axis and a surface of the polarizer at which the incoming light beam is deflected and/or transmitted. Most preferred, the polarizer is tilted in such a way that an angle between the optical emission axis and a surface of the polarizer at which the outgoing light beam is deflected and/or transmitted substantially corresponds to an angle between the optical detection axis and a surface of the polarizer at which the incoming light beam is deflected and/or transmitted. Preferably, the light emitter and the light receiver are substantially equidistantly spaced from the polarizer. Such a substantially symmetric arrangement of the components can further contribute to a compact design of the device geometry.

Preferably, the polarizer is fixed inside the housing at its correct angular position with respect to the emission axis and the detection axis by a holder. The holder preferably comprises at least a plate comprising a recess receiving a lateral edge of the polarizer. Preferably, the holder comprises outer walls arranged substantially in a cuboid shape. The polarizer preferably extends inside the cuboid substantially in a diagonal direction of a base of the cuboid from one corner edge to an opposed corner edge of the cuboid. The height of the corner edges preferably corresponds to the height of the polarizer.

Preferably, the light emitter and the light receiver are mounted on angled faces of a plate. The plate is preferably bent. In particular, a plate comprising a substantially V-shaped bending is conceivable. The bent plate is useful to facilitate a reproducible installation of the light emitter and the light receiver in the device at their correct respective angular orientation and also to stabilize these components in their correct relative position during operation of the device. Preferably, the holder for the polarizer is fixed to the plate in order to also ensure a correct position of the polarizer with respect to the light emitter and the light receiver.

Preferably, the bent plate is a circuit board. The circuit board preferably contains electrical components, in particular to control the light emitter and/or the light receiver and/or to determine and deliver a measurement signal from the light detected by the light receiver to the signal output. By the incorporation of those required components on the mounting plate of the light emitter and the light receiver the device complexity can be further reduced.

The reflector is preferably arranged externally from the housing in which the light emitter and the light detector is arranged. In particular, during operation of the device, the reflector is preferably arranged on an opposed side of a monitored area as compared to the side at which the light emitter and the light detector is arranged. Thus, a light path for the outgoing light beam traversing the monitored area from the light emitter to the reflector and for the reflected light beam retraversing the monitoring area from the reflector to the light receiver can be realized. In this way, an object blocking the light path of the retraversing light beam can be detected. Preferably, the reflector is a retroreflector.

According to a preferred configuration, the reflector is arranged in such a way that the emitted light beam and the reflected light beam propagate along a light path having substantially the same optical axis external from the housing. This can contribute to a facilitated installation and alignment of the housing with respect to the reflector. According to another configuration, the reflector is preferably arranged in such a way that the emitted light beam and the reflected light beam propagate along a light path having a different optical axis external from the housing.

The reflector is preferably adapted to remove the polarization state produced by the polarizer in at least a fraction of the light reflected by the reflector, in particular in at least one of the light transmitted through the polarizer and the light deflected by the polarizer. The polarized light produced by the polarizer is then preferably at least partially or more preferred totally depolarized after its reflection at the reflector. By removing the polarization of the outgoing light beam reflected by the reflector, the returning light beam can thus be distinguished from the outgoing light beam. The distinguishing feature of the returning light beam can be enhanced by the polarizer providing the incoming light beam with a polarization defined by a differing polarization state. Thus, an unambiguous detection of the light beam reflected by the reflector and consequently also any blocking of the reflected light beam, in particular by any object, can by achieved.

According to a first preferred configuration, the reflector is substantially reflective over the complete wavelength range of the light emitted by the light emitter. According to a second preferred configuration, the reflector is wavelength selective and only allows a reflection over a portion of the wavelength range of the light emitted by the light emitter. Preferably, the reflectable wavelength range of the reflector comprises or consists of a UV wavelength range, more preferred a UVB and UVC wavelength range, and most preferred a UVC wavelength range. In particular, a wavelength range below 350 nm, more preferred below 300 nm, and most preferred below 290 nm is conceivable.

BRIEF DESCRIPTION OF THE DRAWINGS

The invention will be described in more detail in the following description of preferred exemplary embodiments with reference to the accompanying drawings. In the drawings.

DESCRIPTION OF PREFERRED EMBODIMENTS

Figure 1:
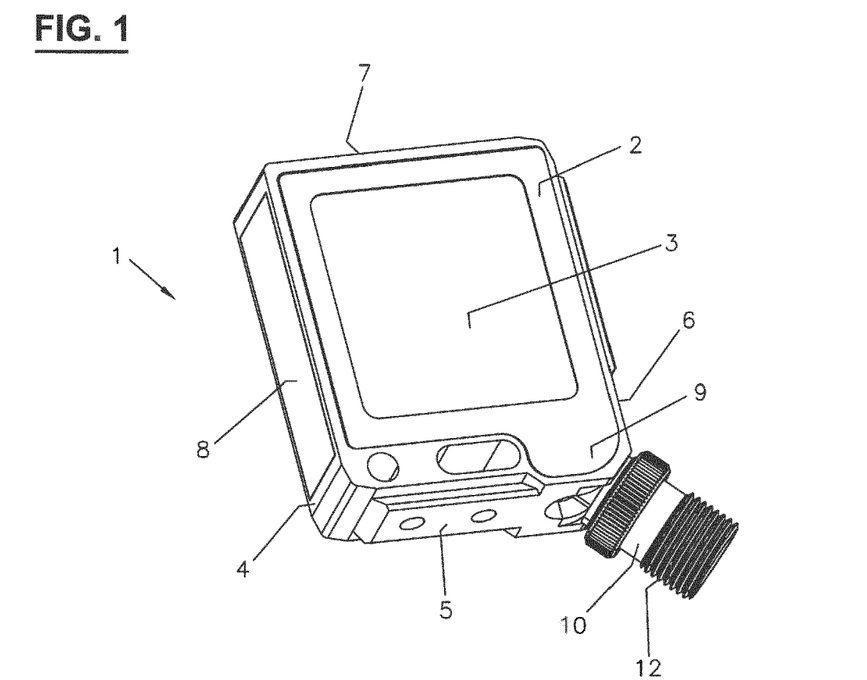
FIG. 1 is a perspective view of a device for emission and detection of polarized light.
Figure 2:
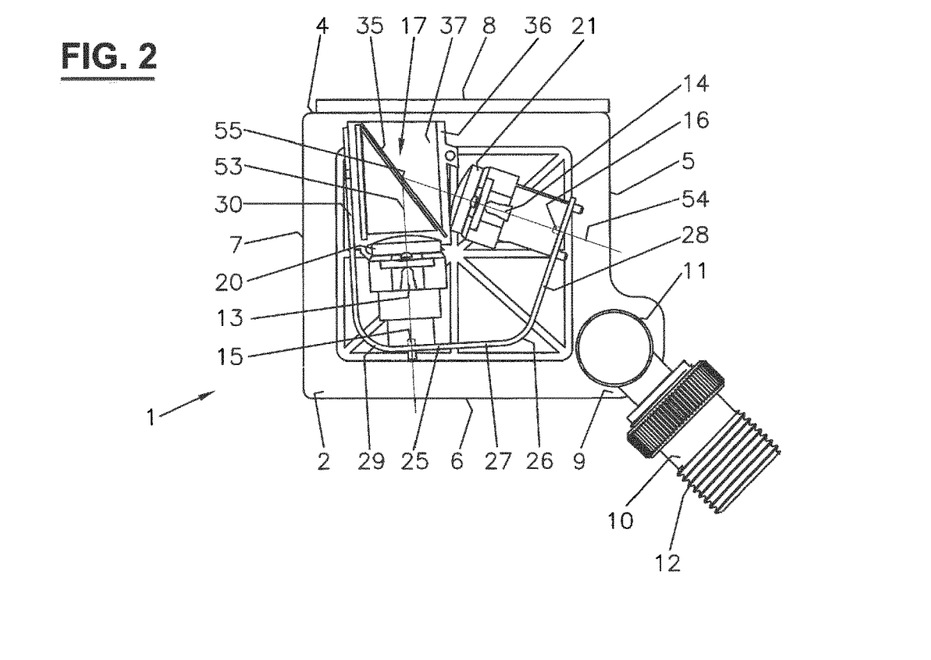
FIG. 2 is a longitudinal sectional view of the device shown in FIG. 1.
Figure 3:
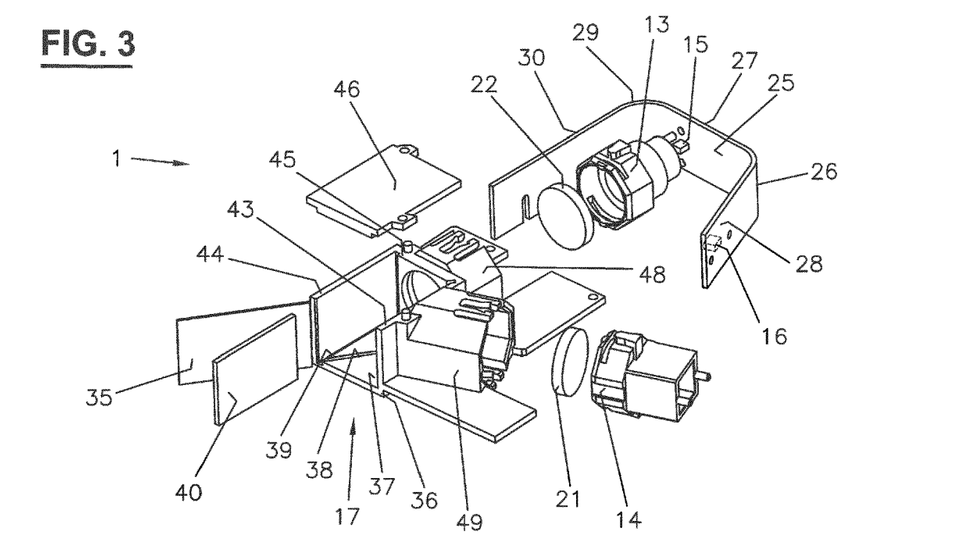
FIG. 3 is an exploded view of components included in a housing of the device shown in FIGS. 1 and 2.

FIG. 1 shows a device 1 for emission of polarized light and its detection. Device 1 comprises a housing 2 containing components required for a generation and emission of a polarized light beam and for a reception and detection of a polarized light beam, as they are depicted in FIGS. 2 and 3.

Housing 2 has the shape of a substantially flat rectangular block comprising two opposing substantially square shaped side walls 3 surrounded by four slimmer face walls 4-7 mutually interconnected in a substantially right angle. A transmission window 8 is arranged in a frontal face wall 4 of cuboid 2. Transmission window 8 is transparent for light having a UVC wavelength. The optical pathways required for directing and receiving an outgoing and incoming light beam through transmission window 8 inside housing 2 substantially extend within a plane parallel to side walls 3. Such an arrangement permits a rather compact and handy size of housing 2.

At a corner region 9 of housing 2 in between a bottom face wall 5 and a rear face wall 6, a fixation arm 10 is attached such that it is pivotable within a plane parallel to side walls 3. A respective pivotable joint 11 is articulated to corner region 9. A thread 12 is disposed at an outer end of fixation arm 10 opposed to pivotable joint 11 and permits a mounting of device 1 on a corresponding support. Thus, fixation arm 10 allows a facilitated installation and alignment of device 1 with respect to the optical settings of an external monitoring area. Fixation arm 10 further includes a power adapter suitable for an electrical power supply of internal components and a signal output for a measuring signal delivered by device 1.

The components enclosed inside housing 2 comprise a light emitter 16, a light receiver 15, and a polarization unit 17. Light emitter 16 is a light emitting diode (LED) having an emission spectrum within a UVC-wavelength range. The peak wavelength of its emission spectrum ranges at ca. 280 nm. It is also conceivable that light emitter 16 is a laser diode emitting at a wavelength within the UVC spectrum. Light receiver 15 is a photodiode comprising a responsivity spectrum in a UVC-wavelength range.

A collimator lens 21 is arranged in the optical path between light emitter 16 and polarization unit 17. Collimator lens 21 is configured to narrow a diverging light beam generated by light emitter 16 down to a substantially parallel light beam before it enters polarization unit 17. A focusing lens 22 is arranged in the optical path between polarization unit 17 and light receiver 15. Focusing lens 22 is configured to focus a light beam down to a smaller spot size after an interaction of the light beam with polarization unit 17 and before its detection by light receiver 15.

By the arrangement of light emitter 16 and collimator lens 21 an optical emission axis 54 is provided along which the light emitted by light emitter 16 propagates. By the arrangement of light receiver 15 and focusing lens 22 an optical detection axis 53 is provided such that light propagating at a light path along optical detection axis 53 can be received by light receiver 15. Optical emission axis 54 substantially extends through the optical center of collimator lens 21. Optical detection axis 53 substantially extends through the optical center of focusing lens 22.

Light emitter 16 and light receiver 15 are mounted on a plate 25. A support 13 for focusing lens 22 and a support 14 for collimator lens 21 are also mounted on plate 25. Supports 13, 14 are substantially cylindrically shaped and carry the respective lens 22, 21 at their front end. Light emitter 16 and light receiver 15 are arranged inside a cavity of the respective support 13, 14 in the center of its rear end. Supports 13, 14 ensure a correct alignment of lenses 21, 22 with respect to light emitter 16 and light receiver 15.

Plate 25 is a circuit board carrying electrical components required to control light emitter 16 and light receiver 15. Circuit board 25 further carries an evaluation circuit configured to process a measuring signal obtained by light receiver 15. Plate 25 comprises a bending 26 at its thinner face such that two angled legs 26, 27 are provided in a V-shaped manner. Thus, inner faces of legs 26, 27 are angled and opposing each other. The angle of bending 26 in between the angled faces is larger than a right angle.

Light emitter 16 and light receiver 15 are respectively mounted on one of legs 26, 27 of bent plate 25 at their angled faces such that optical emission axis 54 of light emitter 16 and optical detection axis 53 of light receiver 15 is substantially oriented orthogonal with respect to the respective face. This implies that the optical emission axis 54 of light emitter 16 and the optical detection axis 53 of light receiver 15 cross each other at an intersection point 55. The angle enclosed at the intersection point in between optical emission axis 54 and optical detection axis 53 substantially corresponds to 180° subtracted by the angle of bending 26. The location of intersection point 55 between optical emission axis 54 and optical detection axis 53 and the angle enclosed in between can thus be set by an appropriate choice of the angle of bending 26 of plate 25.

Bent plate 25 comprises a second bending 29 such that a third leg 30 is constituted. Second bending 29 is substantially rectangular. Polarization unit 17 is mounted on an inner face of third leg 30 which is opposing the inner face of the other two legs 26, 27 of plate 25 and angled with respect to the face of adjacent leg 27. In this way, it can be ensured that polarization unit 17 is maintained in a correct position with respect to intersection point 55 between optical emission axis 54 and optical detection axis 55 and the angle enclosed therein.

Polarization unit 17 comprises a single polarizer 35. Polarizer 35 is constituted by a substantially plate shaped light receiving body. Polarization unit 17 further comprises a holder 36 for polarizer 35. Holder 36 comprises a base plate 37 having a rectangular shape and comprising a recess 38 diagonally extending in between two diametrically opposing corners of base plate 37. Diagonal recess 38 is receiving a lower edge of polarizer 35 and thus maintaining it in its correct position.

Another recess 39 is laterally extending along an outer edge of base plate 37. Lateral recess 39 receives a lower edge of a cushion 40. Cushion 40 is elastic and exposes a front edge of polarizer 35 with a certain amount of pressure further ensuring its correct position. A top plate 46 of holder 36 comprises a diagonal recess corresponding to diagonal recess 38 in base plate 37 for receiving an upper edge of polarizer 35 and a lateral recess corresponding to lateral recess 39 in base plate 37 for receiving an upper edge of cushion 40.

Holder 36 further comprises outer walls 43-45 arranged in a cuboid shape. An intake 48 for light emitter 16 and collimator lens 21 is joined to a front side of an outer wall 45 comprising an opening to allow a light passage inside polarization unit 17. An intake 49 for light receiver 15 and focusing lens 22 is joined to a front side of another outer wall 43 adapted for a light passage out of polarization unit 17. In this way, a further fixation for light emitter 16 and its collimator lens 21 and for light receiver 15 and its focusing lens 22 is provided in order to ensure a correct angular position of the optical emission axis and the optical detection axis with respect to polarizer 35.

Figure 4:
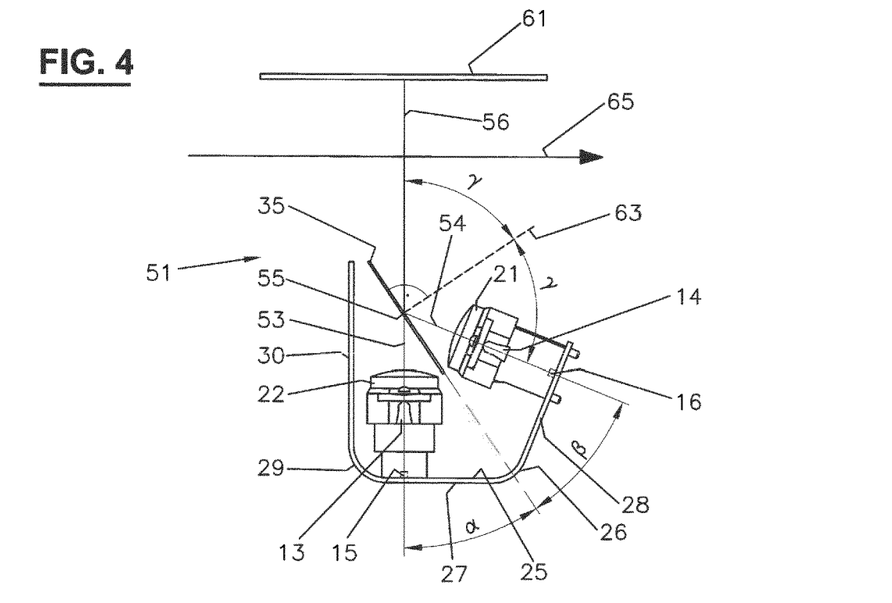
FIG. 4 is a schematic view of a device for emission and detection of polarized light according to a first configuration.

FIG. 4 depicts another device 51 for emission and detection of polarized light. Corresponding features with respect to the device shown in FIGS. 1-3 are denoted with the same reference numerals. Device 51 comprises light emitter 16, light receiver 15, bent plate 25, and polarizer 35 which are arranged in the same manner than in device 1 described above. In addition, device 51 comprises a reflector 61 being adapted to reflect light at least within a spectrum comprising an UVC wavelength range. Reflector 61 is a retroreflector. Reflector 61 may also be included in device 1 described above, wherein it is preferably externally arranged from housing 2.

In FIG. 4, optical emission axis 54 indicating the propagation direction of an outgoing light beam towards polarizer 35 generated by light emitter 16 and optical detection axis 53 indicating the propagation direction of an incoming light beam deflected from polarizer 35 and detectable by light receiver 15 are schematically illustrated. Polarizer 35 is arranged at intersection point 55 of optical emission axis 54 and optical detection axis 53. A light beam is emitted by light emitter 16 along optical emission axis 54 and collimated by collimator lens 21 such that a substantially parallel light beam is formed arriving at polarizer 35. The parallel light beam is deflected at polarizer 35 from optical emission axis 54 to an external optical emission axis 56 utilizing Brewster's angle $\gamma$.

For this purpose, the angle of incidence of the parallel light beam, i.e. the angle in between optical emission axis 54 of the emitted light beam and a perpendicular line 63 on a deflective surface of polarizer 35 on which the emitted light beam is arriving, substantially corresponds to Brewster's angle $\gamma$. During deflection of the incoming light beam, polarizer 35 produces a polarization state defined by an s-polarization of the outgoing light. After deflection, the emergent angle of the outgoing light beam, i.e. the angle in between perpendicular line 63 and external optical axis 56 between polarizer 35 and reflector 61, along which the outgoing light beam propagates, also substantially corresponds to Brewster's angle $\gamma$. An angle $\alpha$ between optical emission axis 54 and the deflective surface of polarizer 35 substantially equals an angle $\beta$ between optical detection axis 53 and the deflective surface of polarizer 35.

The outgoing parallel light beam propagates along external optical axis 56 towards reflector 61. External optical axis 56 is substantially coaxial or parallel with respect to optical detection axis 53. Reflector 61 is arranged in such a way that the reflected light returns at a propagation direction substantially corresponding to external optical axis 56. During reflection, however, the s-polarization is removed from the light beam by reflector 61. Thus, a reflected light beam returning to polarizer 35 is substantially unpolarized. The reflected light beam is substantially parallel and returning to polarizer 35 as an incoming light beam. The incoming light beam is transmitted through polarizer 35 in its parallel form. During transmission of the incoming light beam, polarizer 35 produces a polarization state defined by a p-polarization of the transmitted light. The parallel light beam transmitted through polarizer 35 is then focused by focusing lens 22 and detected by light receiver 15.

In this way, substantially only the fraction of the light emitted by light emitter 16 that has been reflected by reflector 61 and thus depolarized is detectable by light receiver 15. Any other fraction of the emitted light carrying an s-polarization state is not transmitted through polarizer 35 from external optical axis 56 to optical detection axis 53 towards light receiver 15. For instance, a detection of scattered light carrying the s-polarization state of the emitted light can be effectively avoided.

This circumstance can be exploited to detect the presence of an object intransparent to UVC light, such as glass bottles, plastic bottles, pharmaceutical vials, plastic packaging, and transparent foils, which is traveling along a trajectory 65 crossing external optical axis 56. The presence of such an UVC intransparent object within external optical axis blocks the emitted UVC light beam such that it is unable to reach reflector 61. Moreover, a major portion of the emitted light scattered by the UVC intransparent object would still carry the p-polarization state and would therefore not arrive at the position of light receiver 15. Thus, a temporal absence of p-polarized light detected by light receiver 15 is able to indicate a temporal presence of an UVC intransparent object within external optical axis 56.

It is to be noted, that a minor portion of the s-polarized emitted light scattered by a UVC intransparent object may also become unpolarized. The amount of this scattered unpolarized light, however, is usually very small and can be neglected in practice. In general, at least a sharp decline of an s-polarized light detected by light receiver 15 would occur during the crossing of external optical axis 56 by an UVC intransparent object. Such a decline would be sufficient to determine the presence of such an object within external optical axis 56.

In particular, such a UVC intransparent object may comprise a diffusing matter, such as white paper, and/or a reflecting matter, such as glass or plastics material. The reflecting matter may substantially only reflect the light beam without causing any depolarization of the reflected light beam. In consequence, the light beam reflected by such a reflecting matter will be substantially blocked by polarizer 35. The diffusing matter may depolarize the light beam upon its diffusion. The diffused light, however, is characterized by a lower intensity as compared to light reflected by reflector 61. In consequence, the light beam diffused by such a diffusing matter and passing through polarizer 35 will be received by light receiver 15 with a lower intensity allowing a distinction from light returning from reflector 61.

In device 51, as shown in FIG. 4, optical emission axis 54 and optical detection axis 53 are arranged in such a way that they enclose an angle at intersection point 55 substantially corresponding to 180° twice subtracted by Brewster's angle γ. The enclosed angle corresponds to the sum of angle α between optical emission axis 54 and polarizer 35 and angle β between optical detection axis 53 and polarizer 35, i.e. the enclosed angle is α+β and substantially equals 180°-2γ. The reflective surface of reflector 61 is arranged substantially perpendicular with respect to optical detection axis 53. Correspondingly, the reflective surface of reflector 61 is arranged with respect to optical emission axis 54 substantially at an angle of 90° subtracted by the enclosed angle α+β between optical emission axis 54 and optical detection axis 53. Such an arrangement may yield the largest intensity of an emitted light beam reflected by reflector 61 that is detectable by light receiver 15 and thus can be applied to optimize the detection sensitivity.

Figure 5:
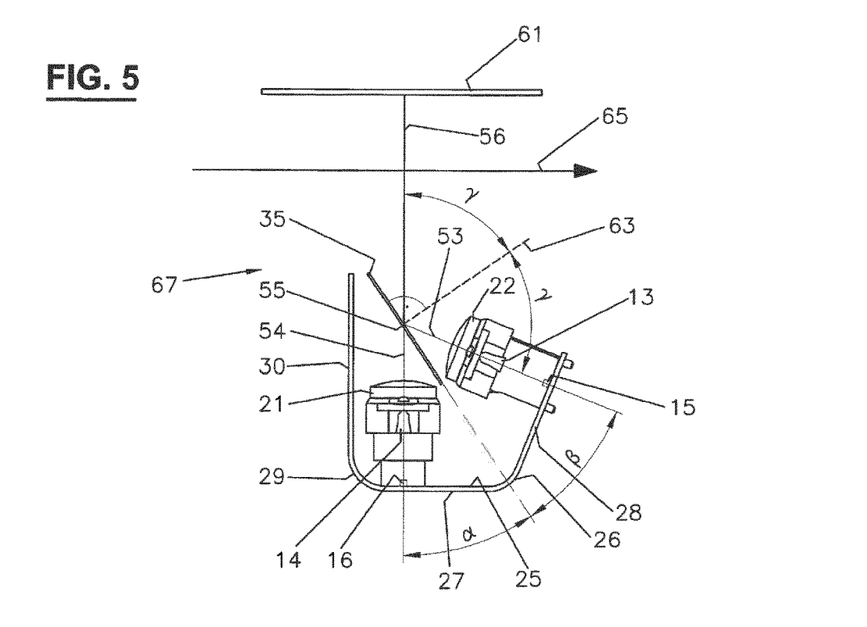
FIG. 5 is a schematic view of a device for emission and detection of polarized light according to a second configuration.

FIG. 5 depicts another device 67 for emission and detection of polarized light. Device 67 substantially corresponds to device 51 shown in FIG. 4, with the exception that the locations of light emitter 16, collimating lens 21, and optical emission axis 54 are switched with the respective positions of light receiver 15, focusing lens 22, and optical detection axis 53. The emission and detection principle of polarized light in device 51 illustrated in FIG. 4 can correspondingly applied in device 67. In this case, the light emitted by light emitter 16 along optical emission axis 54 will be transmitted through polarizer 35 and provided with a p-polarization state. The transmitted light propagates along external optical axis 56 substantially coaxial with respect to optical emission axis 54. After reflection by the reflector 61, the p-polarization is removed and the reflected light returns to polarizer 35 along external optical axis 56.

Upon arrival at polarizer 35, the incoming light beam is deflected from external optical axis 56 towards optical detection axis 53 at Brewster's angle γ. By the deflection, an s-polarization is provided in the incoming light beam. After deflection, the emergent angle of the incoming light beam, i.e. the angle in between optical detection axis 53 and perpendicular line 63, also corresponds to Brewster's angle γ. The deflected s-polarized light then propagates along optical detection axis 53 and is detected by light receiver 15.

Also in device 67, as shown in FIG. 5, optical emission axis 54 and optical detection axis 53 are arranged in such a way that the enclosed angle α+β at intersection point 55 substantially corresponds to 180° twice subtracted by Brewster's angle γ, i.e. α+β substantially equals 180°-2γ. The reflective surface of reflector 61 is arranged substantially perpendicular with respect to optical emission axis 54 and substantially at an angle of 90° subtracted by the enclosed angle α+β with respect to optical detection axis 53. Such an arrangement may be correspondingly applied for optimizing the detection sensitivity.

Figure 6:
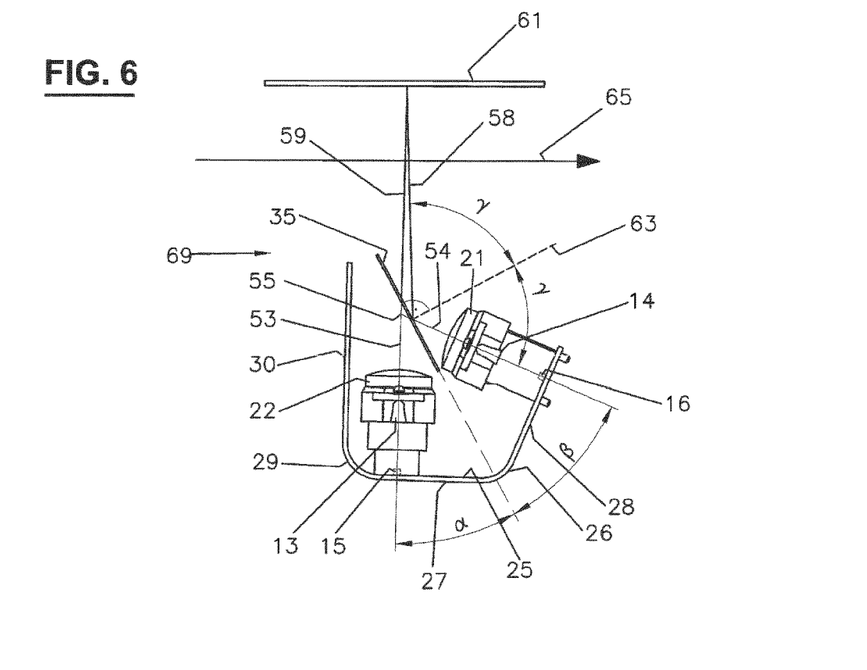
FIG. 6 is a schematic view of a device for emission and detection of polarized light according to a third configuration.

FIG. 6 depicts another device 69 for emission and detection of polarized light. Device 69 substantially corresponds to device 51 shown in FIG. 4, with the exception that an external optical emission axis 58 in between polarizer 35 and reflector 61 of the outgoing light beam does not correspond to an external optical detection axis 59 in between reflector 61 and polarizer 35 of the reflected light beam. In particular, an angle between a reflecting surface of reflector 61 and external optical emission axis 58 deviates from a right angle. An angle between a reflecting surface of reflector 61 and external optical detection axis 58 also deviates from a right angle. Intersection point 55 in between optical emission axis 54 and optical detection axis 53 is shifted from the position of polarizer 35, wherein polarizer 35 is located in proximity to intersection point 55.

Figures 7, 8:
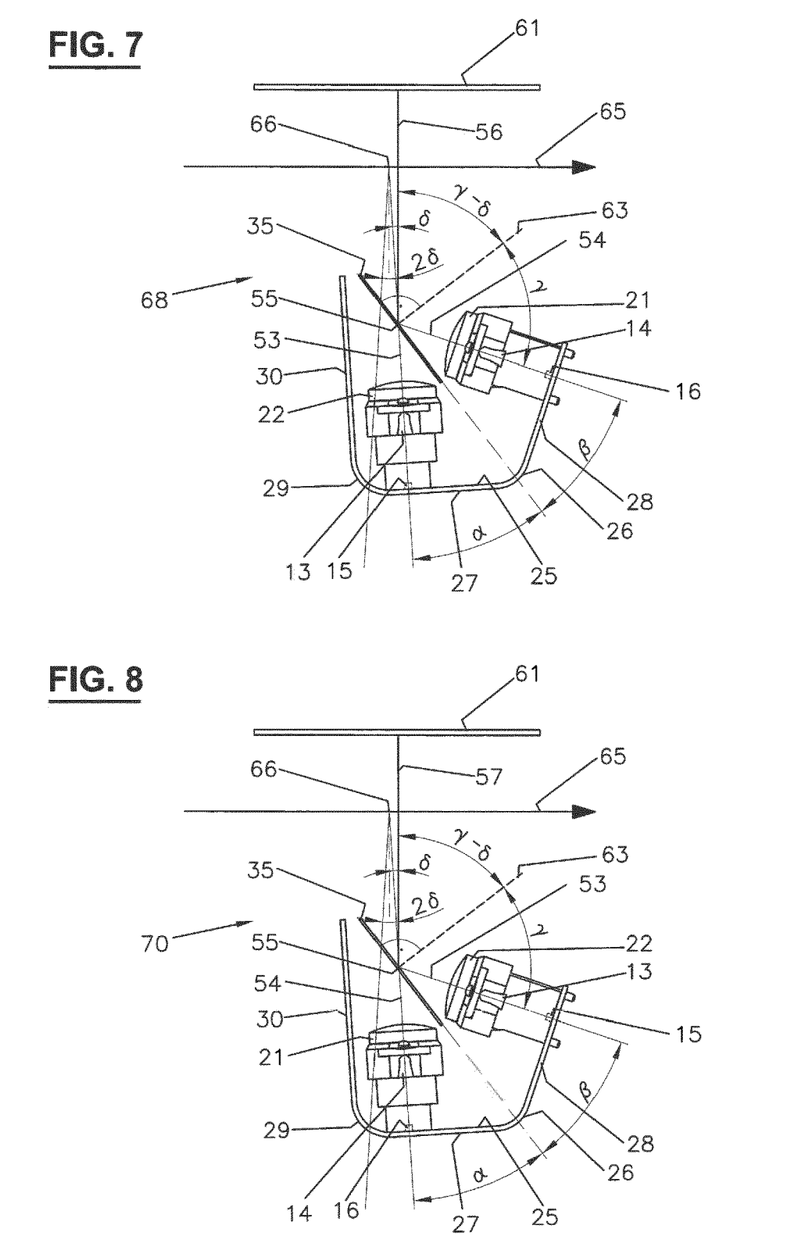
FIG. 7 is a schematic view of a device for emission and detection of polarized light according to a fourth configuration.
FIG. 8 is a schematic view of a device for emission and detection of polarized light according to a fifth configuration.

FIG. 7 depicts a further device 68 for emission and detection of polarized light. Device 68 substantially corresponds to device 51 shown in FIG. 4, with the exception that optical emission axis 54 and optical detection axis 53 are arranged such that the enclosed angle α+β at intersection point 55 is smaller than 180° twice subtracted by Brewster's angle γ by a deviation angle δ, i.e. α+β substantially equals 180°-2γ-δ. The angle between reflective surface of reflector 61 and optical detection axis 53 deviates from a right angle by deviation angle δ. Correspondingly, the reflective surface of reflector 61 is arranged with respect to optical emission axis 54 substantially at an angle of 90° subtracted by the enclosed angle α+β of optical emission axis 54 and optical detection axis 53 and subtracted by deviation angle δ. Deviation angle δ is approximately 3°.

In consequence, the outgoing and incoming light reflected at reflector 61 substantially propagates along a common external optical axis 57 between polarizer 35 and reflector 61, wherein the angle between external optical axis 57 and perpendicular line 63 on the deflective surface of polarizer 35 deviates from Brewster's angle γ by deviation angle δ. Thus, mostly a portion of the emitted light deflected by polarizer 35 at Brewster's angle α subtracted by deviation angle δ does substantially contribute to the incoming light beam being reflected at reflector 61. Correspondingly, since optical detection axis 53 deviates from a coaxial or parallel orientation with respect to external optical axis 57 by deviation angle δ, mostly a portion of the light reflected at reflector 61 being transmitted through polarizer 35 at a transmission angle deviating from external optical axis 57 by deviation angle δ does substantially contribute to the detectable light beam propagating along optical detection axis 53. The optical axis along which the incoming light beam transmitted through polarizer 35 substantially propagates thus may deviate from the orientation of optical detection axis 53 by deviation angle δ, wherein at least a portion of the transmitted light can still be detected by light receiver 15.

By such an arrangement, the detection reliability for the light reflected by reflector 61 can be enhanced. In particular, it can be avoided that light scattered by an object 66 travelling along trajectory 65 crossing external optical axis 57 succeeds to arrive in the detectable light path of light receiver 15 substantially provided by optical detection axis 53. Such a situation is depicted in FIG. 7. A major portion of the emitted light is deflected by polarizer 35 at Brewster's angle γ and arrives at object 66 before it crosses external optical axis 57 along trajectory 65. This major portion of the emitted light, however, is mostly scattered by object 66 at an incidence angle and an emergent angle each substantially corresponding to deviation angle δ and thus fails to arrive within the detectable light path of light receiver 15. A minor portion of the emitted light scattered by object 66 at the crossing point with external optical axis 57 is also not detectable by light receiver 15, in particular due to a much smaller intensity of the light arriving on its surface and/or a further decreased intensity of a portion of scattered light arriving in the detectable light path of light receiver 15.

FIG. 8 depicts yet another device 70 for emission and detection of polarized light. Device 70 substantially corresponds to device 68 shown in FIG. 7, with the exception that the locations of light emitter 16, collimating lens 21, and optical emission axis 54 are switched with the respective positions of light receiver 15, focusing lens 22, and optical detection axis 53. Thus, the angle between reflective surface of reflector 61 and optical emission axis 54 deviates from a right angle by deviation angle δ. Correspondingly, the reflective surface of reflector 61 is arranged with respect to optical detection axis 53 substantially at an angle of 90° subtracted by the enclosed angle α+β of optical emission axis 54 and optical detection axis 53 and subtracted by deviation angle δ. The emission and detection principle of polarized light in device 51 illustrated in FIG. 7 can correspondingly applied in device 70 shown in FIG. 8. As illustrated, mostly a portion of the emitted light transmitted through polarizer 35 at a deviation angle δ from optical emission axis 54 may substantially contribute to the incoming light beam being reflected at reflector 61. In particular, the optical axis along which the outgoing light beam transmitted through polarizer 35 substantially propagates may be substantially coaxial or parallel with respect to optical emission axis 54 and thus may deviate from the orientation of external optical axis 57 by deviation angle δ, wherein at least a portion of the transmitted light propagating along external optical axis 57 can still be reflected by reflector 61 and thus return to polarizer 35 to be deflected at Brewster's angle γ and to be detected by light receiver 15. Such an arrangement may be correspondingly applied for optimizing the detection reliability.

The above described emission and detection principles of polarized light illustrated in FIGS. 4, 5, 6, 7, and 8 can be correspondingly applied in device 1 shown in FIGS. 1-3. With regard to external optical axis 57 of device 68, 70 shown in FIGS. 7 and 8, window 8 of device 1 is preferably provided in such a way that an angle enclosed between optical emission axis 54 and a surface of window 8 transmitted by the outgoing light beam deviates from a right angle substantially by deviation angle δ. Correspondingly, an angle between optical detection axis 53 and a surface of window 8 transmitted by the incoming light beam preferably deviates from a right angle substantially by deviation angle δ. Preferably, the transmitted surface of window 8 is arranged substantially in parallel with respect to the reflective surface of reflector 61. This can contribute to a facilitated alignment of device 68, 70 within a monitoring area.

Figure 9:
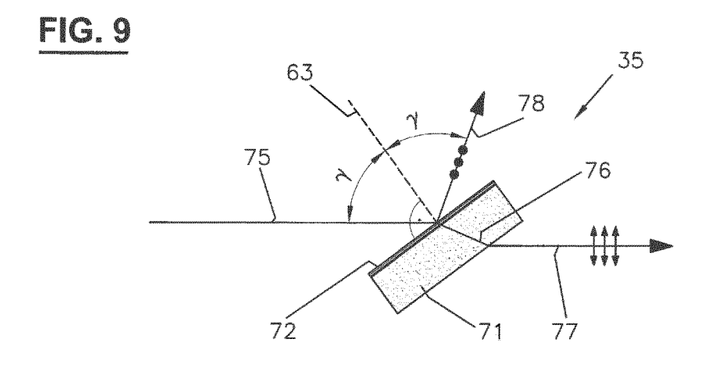
FIG. 9 is a schematic view of a polarizer utilizing Brewster's angle.

FIG. 9 schematically depicts polarizer 35 which is used in devices 1, 51, 67, 68, 69, 70 described above. The polarizer consists of a light receiving body 35 susceptible to receive light substantially over its complete surface and to transmit at least a part of it from a transmitting front surface through its volume to a transmitting back surface and/or to deflect at least part of it from a deflecting surface. At least one of the transmitting front surface and the transmitting back surface constitutes the deflecting surface.

Light receiving body 35 comprises a plate 71 formed by a silicon glass. Glass plate is covered by a multilayer dielectric coating 72. Dielectric coating 72 is applied to provide a reduced or a substantially fully suppressed fraction of unpolarized light being transmitted through polarizer 35 at a desired wavelength range.

Thus, a light beam 75 impinging light receiving body 35 is split apart into a light beam 77 defined by a p-polarization state and a light beam 78 defined by an s-polarization state. S-polarized light beam 78 is deflected from the surface of light receiving body 35 at Brewster's angle γ. The remaining fraction of light beam 75 is substantially transmitted through light receiving body 35 along an angled transmission path 76 due to a differing index of refraction. After transmission, the light transmitted through transmission path 76 results in p-polarized light beam 77 being substantially coaxial or parallel with respect to impinging light beam 75.

Figure 10:
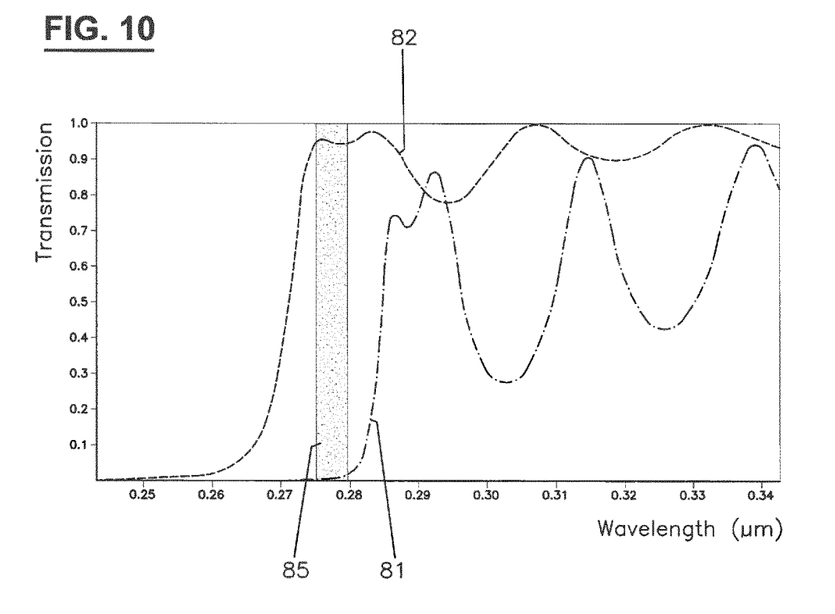
FIG. 10 are functional graphs illustrating the light transmissibility of the polarizer shown in FIG. 5 for differing polarization states of the light over its wavelength.

The described polarization effect over a variable wavelength range is further illustrated in FIG. 10 depicting a functional graph of light transmissibility of polarizer 35 for light having differing polarization states and in dependence of the wavelength of the light. Graph 81 refers to the intensity Ts of transmitted s-polarized light and graph 82 refers to the intensity Tp of transmitted p-polarized light. As can be seen, from the graphs, the light transmission through polarizer 35 strongly depends on the respective polarization state and on the wavelength.

Within a wavelength range 85 in between approximately 275 nm and 280 nm, substantially no s-polarized light is transmitted through polarizer 35. Instead, substantially the complete fraction of the light arriving at the surface of polarizer 35 and carrying an s-polarization state is deflected at the surface of polarizer 35 at Brewster's angle γ. Inversely, a major portion or substantially the whole fraction of the light arriving at the surface of polarizer 35 and carrying a p-polarization state is transmitted through polarizer 35 within wavelength range 85. Thus, the extinction ratio Tp/Ts defined as the ratio between the intensity of p-polarized light Tp and of s-polarized light Ts transmitted through polarizer 35 has a comparatively large value in wavelength region 85. This favorable circumstance can be exploited for an unambiguous detection of the emitted light, as illustrated in the above described device 1, 51.

Figure 11:
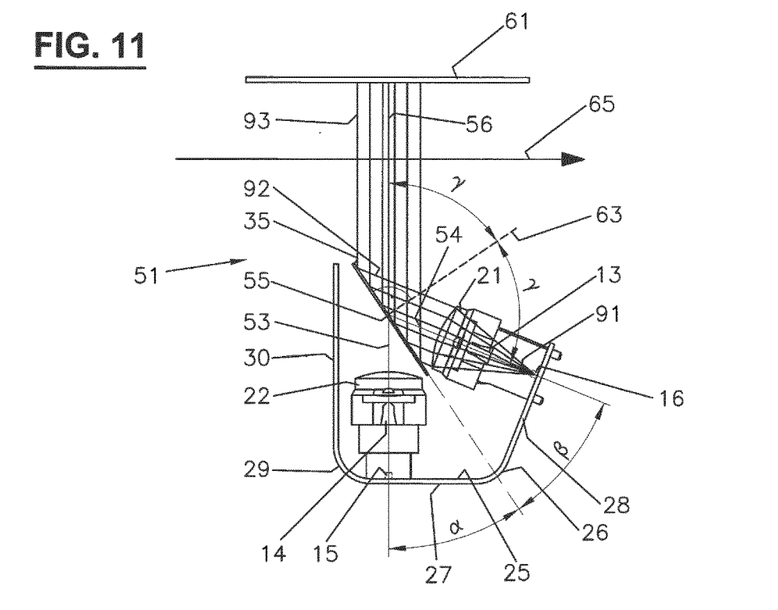
FIG. 11 is a schematic view of the device shown in FIG. 4 illustrating the functionality of a collimator lens in the light path of the emitted polarized light.

FIG. 11 illustrates the functionality of collimator lens 21 in the devices 1, 51, 67, 69, 70 shown in FIGS. 1-8. As an example, device 51 is depicted in FIG. 11. Light emitter 16 produces a divergent light beam 91 that is directed towards collimator lens 21 along optical emission axis 54. In this case, the light provided by light emitter 16 is produced by spontaneous emission processes, in particular from an LED. It is also conceivable, however, that stimulated emission processes are employed for light generation, in particular from an laser diode. Also in the latter case a divergent light beam 91 may be provided along optical emission axis 54.

Figure 12:
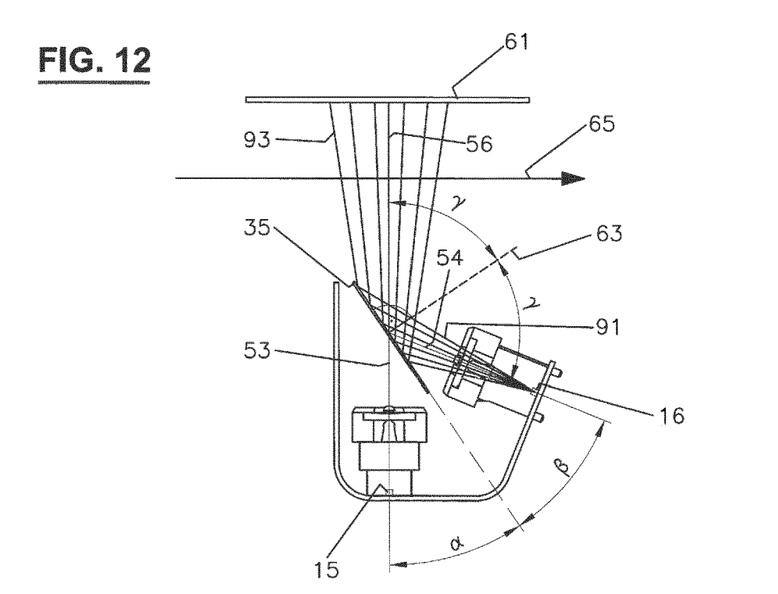
FIG. 12 is a schematic view of the device shown in FIG. 11, wherein the collimator lens is removed.

Collimator lens 21 is arranged in such a way in optical emission axis 54 that divergent light beam 91 is narrowed with respect to the beam size that it would have without collimator lens 21 along its further propagation along optical emission axis 54. This is illustrated in FIG. 12, showing the respective device without collimator lens 21 such that divergent light beam 91 diverges along its propagation along optical emission axis 54 to the position of incidence on polarizer 35 and beyond.

In particular, as shown in FIG. 11, collimator lens 21 is applied such that divergent light beam 91 is transformed into a substantially parallel light beam 92 comprising or substantially consisting of light rays extending substantially in parallel along optical emission axis 54. Parallel light beam 92 comprises a position of incidence on polarizer 35. In the example shown in FIG. 11, the angle of incedence of parallel light beam 92 on polarizer 35 at the position of incidence substantially corresponds to Brewster's angle γ. Different angles of incidence, as employed in devices 68, 69, 70 shown in FIGS. 6-8, can be correspondingly applied. Thus, the arrangement of collimator lens 21 can ensure that substantially all the light rays collimated by lens 21 are impinging on polarizer 35 at substantially the same angle, in particular Brewster's angle γ. Parallel light beam 92 is then at least partially reflected at polarizer 35, wherein an outgoing light beam 93 is provided by this reflected light beam. Outgoing light beam 93 is provided in such a way that it comprises or substantially consists of light rays extending substantially in parallel along external optical emission axis 56.

Figure 13:
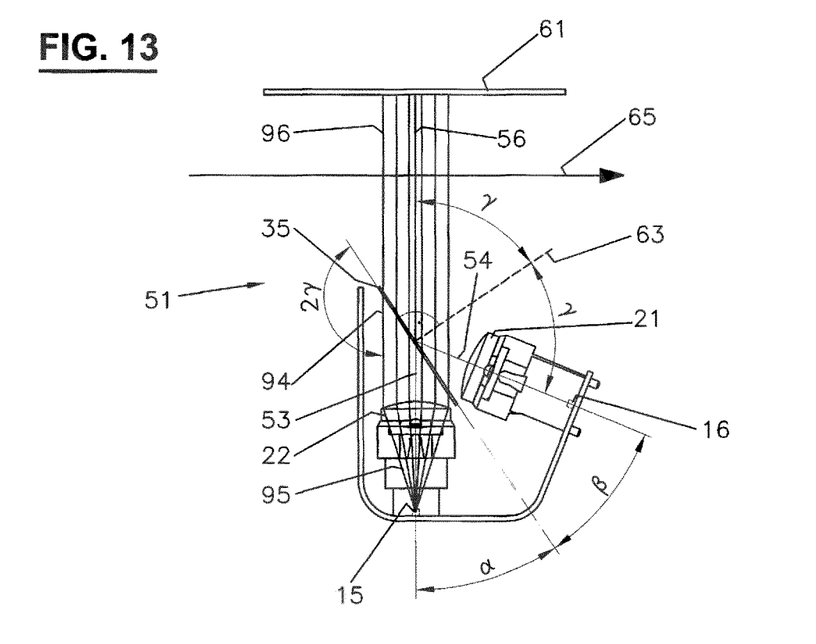
FIG. 13 is a schematic view of the device shown in FIG. 11 illustrating the functionality of a focusing lens in the light path of the detected polarized light.

Correspondingly, as depicted in FIG. 13, focusing lens 22 is arranged in such a way in optical detection axis 53 that an incoming light beam 94, preferably a substantially parallel light beam, is narrowed to a focused light beam 95 with respect to the beam size that it would have without focusing lens 22 along its further propagation along optical detection axis 53 toward light receiver 15. Preferably, incoming light beam 94 comprises or substantially consists of light rays of an external light beam 96 travelling from reflector 61 to polarizer 35, which light beams are transmitting polarizer 35. External light beam 96 is provided in such a way that it comprises or substantially consists of light rays extending substantially in parallel along external optical emission axis 56. In particular, external light beam 96 is produced by a reflection of outgoing light beam 93 on reflector 61. Preferably, focusing lens 22 is applied such that focused light beam 95 is focused on light receiver 15 such that a major part of incoming light beam 94 or substantially all the incoming light is detectable by light receiver 15. In particular, focused light beam 95 may be focused to a substantially point like spot area on light receiver 15 as compared to the spot size of incoming light beam 94.

The above described arrangement of collimator lens 21 and/or focusing lens 22 allows to improve the applicability and the detection reliability of the device 1, 51, 67, 69, 70 in various ways. In particular, a substantially parallel beam shape of the outgoing light beam provided by collimator lens 21 increases the range of coverage and thus the operation distance of device 1, 51, 67, 69, 70 and further contributes to the detection reliability of the incoming light beam by means of an increased quality and thus facilitated detection of the reflected light portion of the parallel outgoing beam 93. A focusing of the incoming light beam 94 provided by focusing lens 22 on light receiver 15 allows to collect the incoming light over an increased collection area and thus further increases the detection reliability.

Collimator lens 21 and/or focusing lens 22 are provided by a plastic lens. The plastic lens may depolarize divergent light beam 91 and/or incoming light beam 94. This depolarization, however, does not restrict the functionality of devices 1, 51, 67, 69, 70 due to the advantageous arrangement of collimator lens 21 in between light emitter 16 and polarizer 35 and/or due to the advantageous arrangement of collimator lens 21 in between light receiver 15 and polarizer 35.

The above described preferred embodiments are intended to illustrate the principles of the invention, but not to limit the scope of the invention. Various other embodiments and modifications to those preferred embodiments may be made by those skilled in the art without departing from the scope of the present invention that is solely defined by the claims.

The invention claimed is:

1. A device for emission and detection of polarized light, the device comprising:
   a light emitter configured to generate an outgoing light beam directed along an optical emission axis,
   a light receiver configured to detect an incoming light beam in an ultraviolet wavelength range directed along an optical detection axis, and
   a polarization unit positioned in the optical emission axis and the optical detection axis and configured to polarize the outgoing light beam and the incoming light beam,
   wherein the optical emission axis and the optical detection axis are angled with respect to one another such that they comprise an intersection point, and
   the polarization unit comprises a polarizer configured to deflect light from at least one of the outgoing light beam away from the optical emission axis and the incoming light beam towards the optical detection axis, said deflected light being defined by a polarization state produced by the polarizer,
   the polarizer comprising a light receiving body utilizing Brewster's angle to produce the polarization state in said deflected light,
   wherein said light receiving body has a transmissible wavelength range comprising the ultraviolet wavelength range,
   wherein a collimator lens is positioned in between the light emitter and the polarizer, and
   a focusing lens is positioned between the polarizer and the light receiver.

2. The device according to claim 1, wherein the polarizer is configured to transmit light in a direction of at least one of towards the light receiver and away from the light emitter, said transmitted light comprising light defined by a polarization state produced by the polarizer differing from the polarization state produced in said deflected light.

3. The device according to claim 1, wherein the collimator lens is configured to produce a narrowed light beam.

4. The device according to claim 1, wherein the polarization state produced in said deflected light corresponds to an s-polarization.

5. The device according to claim 1, wherein the light emitter and the light receiver are arranged in a common housing.

6. The device according to claim 5, wherein the intersection point of the optical emission axis and the optical detection axis is located inside the housing.

7. The device according to claim 1, wherein a housing comprises at least one window transparent for at least one of the outgoing light beam and the incoming light beam.

8. The device according to claim 1, wherein an angle enclosed between the optical emission axis and the optical detection axis at the intersection point deviates from an angle of 180° twice subtracted by Brewster's angle by a deviation angle of at least 1°.

9. The device according to claim 1, wherein said light receiving body comprises at least one layer of a dielectric coating.

10. The device according to claim 1, wherein the polarizer is tilted with respect to the optical emission axis and the optical detection axis in such a way that an angle between the optical emission axis and a surface of the polarizer substantially corresponds to an angle between the optical detection axis and a surface of the polarizer.

11. The device according to claim 1, wherein the device further comprises a reflector configured to reflect the outgoing light beam and to remove the polarization state produced by the polarizer in at least a fraction of the light reflected by the reflector.

* * * * *